US00PP15092P3

(12) United States Plant Patent
Zipperer, III

(10) Patent No.: US PP15,092 P2
(45) Date of Patent: Aug. 24, 2004

(54) GLADIOLUS PLANT NAMED 'WHITE KNIGHT'

(50) Latin Name: *Gladiolus hybrida*
Varietal Denomination: White Knight

(76) Inventor: John O. Zipperer, III, 13590 Brynwood La., Ft. Myers, FL (US) 33912

( * ) Notice: Subject to any disclaimer, the term of this patent is extended or adjusted under 35 U.S.C. 154(b) by 267 days.

(21) Appl. No.: 09/918,660

(22) Filed: Jul. 31, 2001

(65) Prior Publication Data

US 2003/0028942 P1 Feb. 6, 2003

(51) Int. Cl.[7] ..... A01H 5/00
(52) U.S. Cl. ..... Plt./301
(58) Field of Search ..... Plt./301

(56) References Cited

PUBLICATIONS

U.S. patent application Ser. No. 09/745,086, Zipperer, III, filed Dec. 20, 2000.
U.S. patent application Ser. No. 09/742,726, Zipperer, III, filed Dec. 20, 2000.
U.S. patent application Ser. No. 09/877,571, Zipperer, III, filed Jun. 8, 2001.
U.S. patent application Ser. No. 09/877,572, Zipperer, III, filed Jun. 8, 2001.
U.S. patent application Ser. No. 09/877,573, Zipperer, III, filed Jun. 8, 2001.
U.S. patent application Ser. No. 09/877,574, Zipperer, III, filed Jun. 8, 2001.
U.S. patent application Ser. No. 09/877,575, Zipperer, III, filed Jun. 8, 2001.
U.S. patent application Ser. No. 09/918,662, Zipperer, III, filed Jul. 31, 2001.
U.S. patent application Ser. No. 09/918,663, Zipperer, III, filed Jul. 31, 2001.

*Primary Examiner*—Bruce R. Campell
*Assistant Examiner*—Anne Marie Grünberg
(74) *Attorney, Agent, or Firm*—Hahn Loeser & Parks LLP; Laura G. Barrow

(57) ABSTRACT

A new and distinct gladiolus variety, designated 'White Knight', is shown and described. The variety has a light green color (Yellow Green Group 145D) deep within the throat, followed by a pure white color throughout the rest of the petals (White Group 155D). The variety can maintain six to seven florets in open bloom simultaneously in a vase of water and is an excellent opener after transport.

2 Drawing Sheets

The present invention comprises a new and distinct variety of a *Gladiolus hybrida* referred to by the variety name 'White Knight.'

BRIEF DESCRIPTION OF THE PHOTOGRAPHS

ASEXUAL REPRODUCTION

The new variety was originated by the Applicant in a controlled proprietary breeding program in Ft. Myers, Fla. wherein selected gladiolus varieties were crossed (the Applicant's selected provisional breeder's designation is 5-22). The female parent was an unpatented gladiolus variety named 'Dr. Magie', characterized in part by having a small pink bloom, a short stem having a short flower head, and high resistance to Fusarium fungi species. The male parent was a white gladiolus variety named 'T-200,' an unpatented, released variety by Turk characterized in part by having a harvesting time of 76 days, a flower head consisting of 14 to 16 florets, and a stem diameter of 1.0 cm. The seeds were planted in Ft. Myers, Fla., and the selection of the 'White Knight' variety was made in Spring 1988. Asexual reproduction of the 'White Knight' variety was achieved by collecting cormels from the first corm and growing said cormels to maturity in Ft. Myers. All subsequent asexual reproductions of the 'White Knight' variety remain true to the original variety type.

BOTANICAL DESCRIPTION

Figure 1:
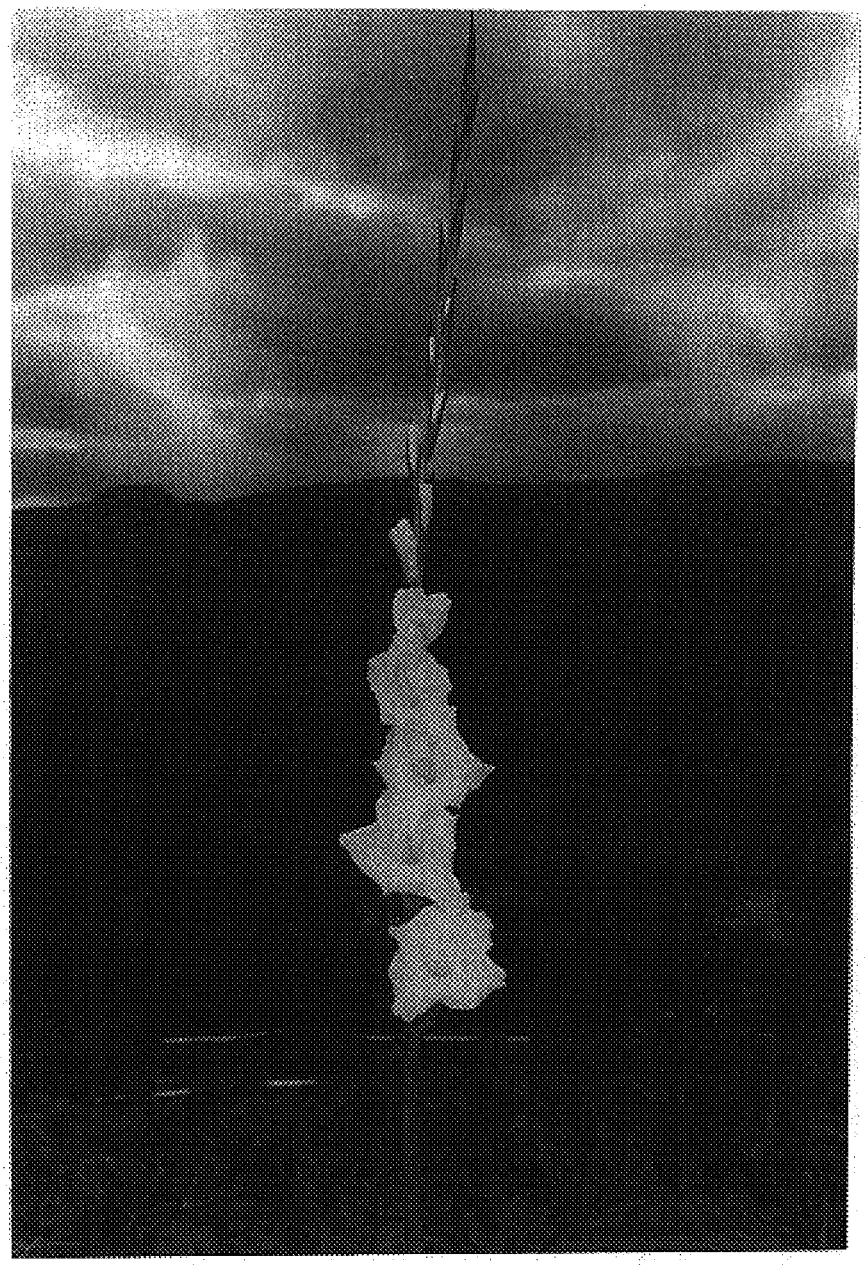
FIG. 1 is a photograph of a 'White Knight' variety plant in bloom.
Figure 2:
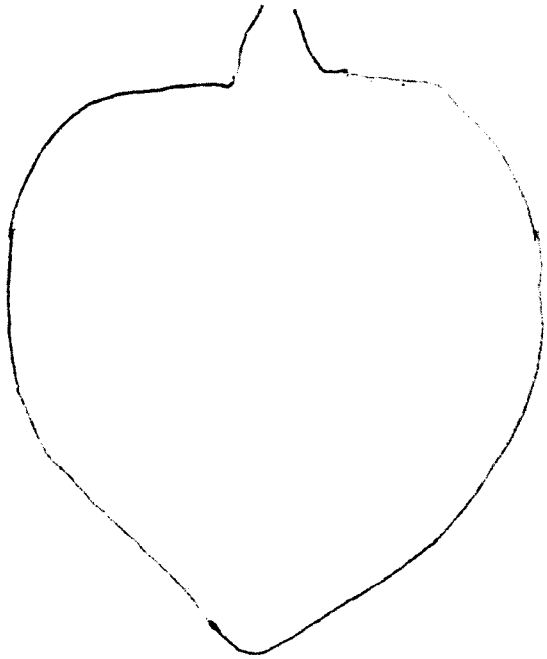
FIG. 2 is a drawing illustrating the shape and size of the large petals.

The accompanying color photograph (FIG. 1) shows the inflorescence and various stages of blooming of the 'White Knight' variety plant.

The following botanical description, except for color, of the 'White Knight' variety was observed when the plant was 76 days old grown under the following conditions in Ecuador:

1) Twelve-hour daylight days with high light intensity;
2) Temperatures: 58–60° F. (low's) and 69–75° F. (high's);
3) Humidity: 50–55%
4) Rainfall: 2–3 inches/month.

All color descriptions with respect to parts of the variety, where color is a distinguishing feature, are made to The Royal Horticultural Society Colour Chart (R.H.S.), except where terms of ordinary usage and dictionary meaning are used. Color observations with respect to The R.H.S. Colour Chart were made in the Netherlands under similar environmental conditions as described above, but at increased day lengths of 12 to 17 hours and 50% to 65% humidity.

The spike of the plant is about 124 cm and contains 18–19 florets when grown from Jumbo size corms (1.75 inch and larger) in Ecuador. The stem color is Yellow Green Group 144C. The stem diameter is 1.5 cm. The head length is about 58 cm, and the bloom diameter is 12 cm. It should be noted, however, that various factors will affect spike length, including temperature (larger spikes occur in cooler weather), irrigation, light intensity, fertilization, soil type (larger spikes occur in heavy soils versus sandy soil), and bulb size (larger bulbs result in larger spikes).

The leaf color of the 'White Knight' variety is Green Group 137C on both sides. The leaf size is about 70 cm (length) by 3.2 cm (width).

The bud size of the 'White Knight' variety is about 8 cm in length. The flowers of the variety each consist of a total of six petals, namely three large petals located on the top half of the flower, a medium-size petal positioned on the lower half of the flower (at 6:00), and two small petals also located on the lower half of the flower (at 4:00 and 8:00). Some flowers of the variety have been observed having five large petals and one small petal. In another arrangement, the variety consists of three large petals located in the upper half of the bloom (between 10:00 and 3:00), two medium-sized petals on the lower half of the bloom (between 4:00 and 9:00), and one small petal near the bottom of the bloom (between 5:00 and 8:00). The variety bloom has a light green color (i.e. Yellow Green Group 145D) deep in the throat, followed by a pure white color throughout the rest of the petals (i.e. White Group 155D for the bloom in open perfect condition and open going down). The color of the bloom tight (i.e. closed) is Green White 157A.

The variety has three stamens and one pistil. The color of the pistil head and stem is White Group N155D. The color of the stamen head on one side is Yellow White Group 158C and White Group N155D on the other side of the head. The color of the stamen stem is White Group N155A.

The corms of the 'White Knight' variety are typical for the gladiolus and have a Yellow Orange Group 14A color under the husk on the top of the bulb one day after harvest.

GENERAL OBSERVATIONS

Compared to the parent 'T-200,' which is the variety most similar to 'White Knight', both the 'White Knight' variety and 'T-200' variety take about 76 days to harvest in Ecuador. Both the 'White Knight' and 'T-200' varieties prefer longer day lengths, do not grow well in the mid-winter, have good tolerance to heat, and have good resistance to bacterial neck rot.

The 'White Knight' variety usually produces one to two stems per Jumbo size corm. The variety can maintain six to seven florets in open bloom simultaneously in a vase of water and can be harvested with one flower showing color. The variety is an excellent opener after transport, in that the stems may be cut tight, shipped dry for a week, and still bloom well afterwards. The variety takes about 3 days to open the first bloom from a stem showing color on only one floret after placement in water. The bloom thereafter holds open for another three days. The stem continues to open for a total of 14 days. Every floret on the stem opens in this variety.

The 'White Knight' variety is much more resistant to attack by Fusarium fungi than the 'T-200' variety. Unlike the 'T-200' variety, the 'White Knight' variety does not have the tendency of producing blind stems in the fall when a bulb has been used two to three times for subsequent asexual reproductions.

The variety does not emit a fragrance.

Compared to the 'T-200' variety, the 'White Knight' variety contains 1 to 2 more florets per flower head, can hold open 1 to 2 more florets, has a stem length that is about 10 cm longer, has a greater stem diameter, and has a flower diameter that is 1 to 1.5 cm larger. Also, unlike the 'T-200' variety, the bottom floret of the 'White Knight' variety often protrudes out to one side more.

Compared to the parent 'Dr. Magie,' the 'White Knight' variety has a bloom diameter that is 1 to 2 cm larger and stems that are about 0.5 cm thicker and 10 to 15 cm longer.

I claim:

1. A new and distinct gladiolus variety of plant, 'White Knight', as shown and described herein.

* * * * *